United States Patent [19]

Rokach et al.

[11] 4,094,986

[45] June 13, 1978

[54] 2-R-SUBSTITUTED-1,2,5-THIADIAZOLE-3-ONE ANTIMICROBIALS

[75] Inventors: Joshua Rokach, Chonedey-Laval; Grant W. Reader, Montreal, both of Canada

[73] Assignee: M. S. & D. (I.A.) Corp., Rahway, N.J.

[21] Appl. No.: 813,015

[22] Filed: Jul. 5, 1977

Related U.S. Application Data

[63] Continuation-in-part of Ser. No. 684,137, May 7, 1976, abandoned.

[51] Int. Cl.$^2$ .................. C07D 285/10; A61K 31/425
[52] U.S. Cl. ................................. 424/270; 260/302 D
[58] Field of Search ..................... 424/270; 260/302 D

[56] References Cited

U.S. PATENT DOCUMENTS

| | | | |
|---|---|---|---|
| 3,763,176 | 10/1973 | Kohn et al. | 260/302 D |
| 3,854,000 | 12/1974 | Kohn et al. | 424/270 |

*Primary Examiner*—Richard J. Gallagher
*Attorney, Agent, or Firm*—Edmunde D. Riedl; Julian S. Levitt

[57] ABSTRACT

2-R-substituted-1,2,5-thiadiazole-3-ones have broad spectrum antibacterial and antifungal activity. They are especially useful in agriculture to protect plants against diseases such as leaf, stem, and fruit spotting, internal discoloration and decay of fruits and vegetables. These compounds are particularly active against diseases caused by the genera Pseudomonas, Xanthomonas, Erwinia, and Corynebacterium.

14 Claims, No Drawings

2-R-SUBSTITUTED-1,2,5-THIADIAZOLE-3-ONE ANTIMICROBIALS

This application is a continuation-in-part application of U.S. Ser. No. 684,137 filed May 7, 1976 now abandoned.

This invention relates to a new class of antibacterial and antifungal compounds, particularly 2-R-substituted-1,2,5-thiadiazole-3-ones. Although derivatives of 1,2,5-thiadiazoles are known, for instance, U.S. Pat. Nos. 3,854,000 and 3,763,176, such compounds must necessarily have a halogen in the 4-position. The compounds of this invention are halogen free.

The 2-R-substituted-1,2,5-thiadiazole-3-ones of this invention have the structural formula:

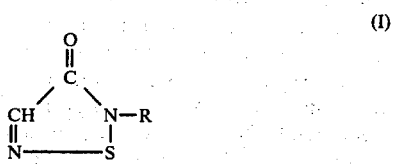

where R is a hydrocarbon group of from 1–16 carbon atoms including $C_1$ to $C_{16}$ alkyl, phenyl-$C_1$ to $C_{10}$ alkyl, and phenyl. In general, it is preferred that the hydrocarbon group R contain from 6–14 carbon atoms, $C_{12}$ alkyl and benzyl being the most preferred groups. The term "alkyl" includes straight or branched hydrocarbon radicals. R includes, for example, methyl, ethyl, propyl, isopropyl, butyl, sec-butyl, t-butyl, pentyl, 1-(2-ethyl)-propyl, hexyl, 1-(2,3-dimethyl)butyl, heptyl, 1-(2-ethyl-4-methyl)butyl, octyl, nonyl, decyl, dodecyl, hexadecyl, 4-t-butylphenyl, 2,4-diethylphenyl, 4-ocylphenyl, 3-heptylphenyl, 4-hexylphenyl and 2,4,6-triethylphenyl.

The compounds of this invention are prepared by reacting an amide of formula II with at least one mole of sulfur monohalide, $S_2X_2$, where X is bromine or chlorine.

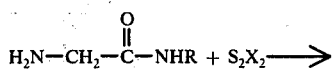

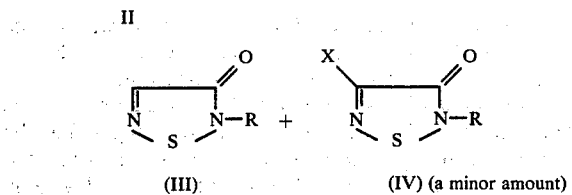

The reaction is conducted in any inert solvent such as dimethylformamide or hexamethylphosotriamide at a temperature of from about $-10°$ to $60°$ C. for from about 10 to 18 hours.

The molar ratios of glycine R-substituted amide free base or salt to $SX_2$ can range from 1:2 to 1:5 although a molar ratio of 1:3 is most satisfactory.

After reaction is complete, the solvent is stripped under vacuum.

The 2-R-substituted-1,2,5-thiadiazole-3-ones are neutral compounds readily extractable from acidic or basic mixtures.

The rather minor quantities of compound IV produced in the preparation of product III can be removed by usual techniques such as distillation, crystallization as well as column chromatography.

The following examples are presented to illustrate the invention but should not be construed as limitations thereof.

EXAMPLE I 2-n-Dodecyl-1,2,5-thiadiazole-3-one

N-n-Dodecyl-2-aminoacetamide.HCl (23.55 g., 84.6 mmoles) is added in portions over 45 minutes to a stirred solution of sulfur monochloride (34.8 g., 258 mmoles) dimethylformamide in 75 ml. (DMF), maintaining the reaction temperature between $5°-8°$ C. During the addition, the mixture became quite thick and 25 ml. DMF is added. After the addition is complete, another 25 ml. DMF is added and the reaction mixture allowed to warm to room temperature and stirred for 18 hours. The reaction mixture is poured into 1 liter water and extracted three times with 300 ml. ether. The ether is dried ($Na_2SO_4$) and evaporated to dryness. The solid residue was chromatographed on silica gel to afford 18.44 g. of 2-n-dodecyl-1,2,5-thiadiazole-3-one (81% yield), m.p. $68°-70°$ C. (hexane).

Analysis calculated for $C_{14}H_{26}N_2OS$: C, 62.18; H, 9.69; N, 10.36; S, 11.85. Found: C, 62.37; H, 9.53; N, 10.50; S, 12.00.

The above procedure is general for the preparation of the 2-$C_1$ to $C_{16}$-R-substituted-1,2,5-thiadiazole-3-ones of this invention and the entire range of products are obtained by employing 2-$C_1$ to $C_{16}$-R-substituted-2-aminoacetamide in analogous molar quantities to the N-n-dodecyl2-aminoacetamide.

TABLE I

| REACTANTS R-2-aminoacetamide | $S_2X_2$ | Product R |
|---|---|---|
| $H_2NCH_2CONHCH_2\phi$ . HCl | $S_2Cl_2$ | $-CH_2\phi$ |
| $H_2NCH_2CONHCH_3$ . HCl | $S_2Cl_2$ | $-CH_3$ |
| $H_2NCH_2CONH\phi$ . HCl | $S_2Cl_2$ | $-\phi$ |
| $H_2NCH_2CONH_2CH_2CH_2CH_3$ . HCl | $S_2Cl_2$ | $-CH_2CH_2CH_3$ |
| $H_2NCH_2CONH_2CH-(CH_3)_2$ | $S_2Cl_2$ | $-CH(CH_3)_2$ |

The N-substituted-2-aminoacetamides intermediates, required for the synthesis of the 2-substituted-1,2,5-thiadiazole-3-ones, can be prepared by standard methods (James R. Vaughan, Jr., and Ruth L. Osato, J. Amer. Chem. Soc., 74, 676 (1952), and Miklos Bodansky and Vincent Du Vigneaud, J. Amer. Chem. Soc., 81, 5688 (1959)). The following example for N-n-dodecyl-2-aminoacetamide hydrochloride is typical.

EXAMPLE II

N-n-Dodecyl-2-aminoacetamide Hydrochloride

Step A: N-Benzyloxycarbonyl glycine (209.2 g., 1 mole) is suspended in 600 ml. $CHCl_2$ and 140 ml. triethylamine is added. A solution gradually results. This mechanically stirred solution is cooled in an ice-salt bath and ethyl chloroformate (110 g., 1 mole) is added dropwise over 45 minutes, keeping the temperature at $0°-3°$ C. The resulting mixture is stirred in the cold an additional $\frac{1}{2}$ hour. A solution of n-dodecylamine (185.4 g., 1 mole) in 250 ml. $CH_2Cl_2$ is added dropwise, keeping the temperature below $10°$ C. After the addition, the mixture is allowed to come to room temperature and stirred for 20 hours; diluted with 500 ml. $CH_2Cl_2$ and washed with water, then diluted NaOH, then water, dried and evaporated to dryness. The residual solid is suspended in 1 liter petroleum ether (30°–60° C.) and boiled for 15 minutes, cooled and filtered, yielding 228.3 g. of N-n-dodecyl-(2-benzyloxycarbonylamino)acetamide, m.p. 112°–115° C. (dec.) (benzene-petroleum ether).

Analysis calculated for $C_{12}H_{36}N_2O_3$: C, 70.18; H, 9.64; N, 7.44. Found: C, 69.76; H, 9.26; N, 7.56.

Step B: 10 G. of N-n-dodecyl-(2-benzyloxycarbonylamino)acetamide is suspended in 200 ml. MeOH and 1 g. 10% Pd/charcoal hydrogenated until no more $H_2$ is absorbed. The resulting suspension is acidified with 3 ml. concentrated HCl and filtered. The solution is concentrated under vacuum until the product begins to crystallize. It is warmed to dissolve the solid and ether added to induce crystallization. This is filtered to yield N-n-dodecyl-2-aminoacetamide hydrochloride (5 g.) as white crystals, m.p. 200° C.

Analysis calculated for $C_{14}H_{30}N_2O \cdot HCl$: C, 60.30; H, 11.21; N, 10.04; cl, 12.71. Found: C, 60.49; H, 11.27; N, 10.23; Cl, 12.94.

In an analogous manner $C_1$–$C_{16}$-alkylamines can be substituted for a similar molar quantity of the n-dodecylamine to prepare the entire range of the compounds of this invention. Thus, substituting respectively benzylamine, methylamine, aniline, 2-aminopropane and 1-aminopropane for the n-dodecylamine there is obtained N-benzyl-2-aminoacetamide . HCl; N-methyl-2-aminoacetamide . HCl; N-phenyl2-aminoacetamide . HCl; isopropyl-2-aminoacetamide . HCl; and N-propyl-2-aminoacetamide . HCl.

The compounds of our invention are broad spectrum antibacterial and antifungal agents. For use, the compounds described herein can be applied neat or employed in a diluted form. Satisfactory diluents include any inert material not destructive of the antimicrobial activity and especially liquid formulations comprising aqueous dispersions, solutions, and emulsions. Solid diluents include talc, corn starch, alumina and diatomaceous earth. The antimicrobial agents of this invention can also be deposed on materials such as natural fibers including paper, cotton, wool and synthetic fibers such as nylon, polypropylene, as well as upon inanimate surfaces including hard surfaces such as wood, glass, metal, tile, rubber, plastic, and porous surfaces such as concrete, leather and the like.

Another application is alone or in solution or suspension or in conjunction with soaps or detergents for use in cleansing the skin, particularly in presurgical scrubbing formulations, or in formulations for controlling the growth of *Corynebacterium acnes*. *C. acnes* is a strain of bacteria implicated in acne conditions, especially *Acne vulgaris*, wherein applications of as little as 1 to 5 ppm. is effective in controlling such skin dwelling bacteria. Larger concentrations can be used, if desired, without irritation or discomfort such as 2500 ppm and higher. Where the cleansing formulation is diluted with water upon use, the formulation can comprise from 0.01% by weight and more of the compounds of this invention.

In addition, the compounds described herein can be employed in impounded water, such as swimming pools, ponds or industrially-used water such as papermill water to inhibit growth of undesirable bacteria, fungi, and/or algae at levels as low as 0.5–5 ppm.

In the control of slime-producing microorganisms and algae in recirculating industrial waters, particularly cooling operations and especially installations such as cooling towers, the compounds of this invention are usually employed alone, but can also be used in combination with other antimicrobial agents. Concentrations in the recirculating water of as little as $1 \times 10^{-4}\%$ by weight are effective in inhibiting microbial growth. To insure effectiveness, especially against more resistant strains of microorganisms, and also when make-up water is added to replace water lost by evaporation and the like, concentrations of from $1 \times 10^{-4}\%$ to $5 \times 10^{-2}\%$ by weight are most satisfactory. Dosage may be continuous or as intermittent "shock treatment", i.e., addition in a 10–20 minute period every 4–8 hours. They are especially useful against bacteria and fungi responsible for stunting the growth and even destruction of many types of crop-producing plants. In agriculture, severe problems are faced in the raising of cotton, beans, corn and other crops because of the loss of yield per acre due to the action of soilborne fungi on seed and on the roots of the young plants. Control or elimination of these losses can be accomplished by the use of the compounds herein described as soil disinfectants in accordance with the invention. They can also be used for the control of bacterial and fungal diseases on trees and stored crops.

In formulating the compounds of this invention for the above uses, these compounds can be employed in combination with other antimicrobial agents, surfactants, insecticides, defoamers, odorants, or as chelates of metals such as copper, calcium, magnesium and iron.

Wettable powder formulations for use as a dispersant in water represent a practical means for good distribution in soil. Other methods of achieving the same results include the preparation of dusts. All of the thiadiazole-3-ones can be blended as fine powders with the commonly used powder diluents such as talc, clay refined silicates, wood flour, sand, magnesium oxide, calcium carbonate, fuller's earth, kaolin, diatomaceous earth, mica, pumice and the like. The powder can have the following formulation:

|  | Percent |
| --- | --- |
| R-Substituted-1,2,5-thiadiazole-3-one | 1–75 |
| Inert Diluent (clay, talc, etc.) | 25–99 |

The mixtures may be finely powdered, e.g., to the 1–10 micron average particle size, or be made by blending the already finely powdered ingredients.

For application as agricultural disinfectants the dusts may be applied to the seed and surrounding soil at the time of planting. The concentration of the sterilant is adjusted to give an effective, nonphytotoxic dosage in the soil. In general, the soil concentration should be from 10 to 25 parts per million (of active ingredient). For most economical and effective use the dusts can be applied in bands of 6 to 8 inches centered on the rows just prior to seeding. The material can then be rototilled to a depth of several inches. This mode of treatment saves material and protects the root system of young plants against microbial attack. For the protection of a given crop, such as cabbage, the band spread of antimicrobial can vary from 8 inches for black root disease to 12–15 inches for club root disease prevention. Similarly, the depth to which the fungicide should be distributed can vary from 2 to 6 inches.

The wettable powders can be prepared by the addition of 0.1–5% of a wetting agent to the powder blends.

Many dispersing agents are commercially available which are nonphytotoxic at the required concentrations. These may, for example, be alkali metal and amine salts of sulfated and sulfonated acids, alcohols, and oils, or polyethoxylated alkyl phenols, long chain fatty amine quaternary salts, partial phenols, long chain fatty amine quaternary salts, partial fatty acid esters of polyhydric alcohols, etc. Some dispersants can be used in preparing emulsifiable concentrates of the polyamines in organic solvents. Many of these agents are available in solvent-soluble form. The manner of application to the soil is similar to the dusts. Spray equipment is used to spread the suspensions or emulsions over the soil and by discing, the fungicidal agents can be uniformly distributed to varying depths. Spray application is also effective for band-limiting the dosages.

Other agricultural uses for these formulations involve the eradication of bacterial blights of plants by application to the involved surface areas. The compounds of this invention show high orders of bacterial inhibition and are especially useful for this purpose. Some of the diseases which are of commercial importance in decreasing yield and quality and are controlled by the compositions of the invention are fire blight of apple and pear, bacterial spot on stone fruit, cherry leaf spot, walnut blight, common blight of bean, bacterial spot of tomato and pepper, and potato seed piece decay. The effective concentration of R-substituted-1,2,5-thiadiazole-3-one required varies from 5–200 parts per million parts of the material to be protected. They may be applied as dusts, powder dispersions in water as emulsions in water, or as aqueous dipping baths. Other plant diseases which can be controlled by treatment with these formulations are fungal in origin, such as the many kinds of powdery mildew and leaf scabs.

For seed treatment, proportions as low as 1 to 4 ounces per hundred weight (550 to 600 ppm on seed) are effective against various fungi.

The compounds of the invention can be used in form of aqueous suspensions or emulsions, the base products being generally insoluble in water. For this type of formulation various powdered carriers can be employed to aid in achieving uniform distribution. Talc, fuller's earth, calcium silicate, calcium carbonate, clays and the like are admixed with the agent along with wetting and dispersing agents and sticking agents. For maximum chemical compatability those which are nonionic in character are preferred. Other nonionic or cationic surfactants are also satisfactory.

What is claimed is:

1. A compound of the formula:

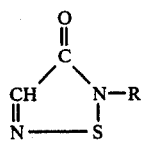

where R is an alkyl group of from 1 to 16 carbon atoms, benzyl or phenyl.

2. A compound according to claim 1 where R is an alkyl group.
3. A compound according to claim 1 where R is phenyl.
4. A compound according to claim 1 where R is benzyl.
5. A compound according to claim 1 where R is dodecyl.
6. A compound according to claim 1 where R is N-propyl.
7. A compound according to claim 1 where R is isopropyl.
8. A composition for inhibiting growth of bacteria and fungi on agriculturally desirable plants and crops comprising a microbiologically effective amount of a compound of the formula:

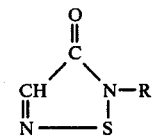

where R is an alkyl group of from 1 to 16 carbon atoms, benzyl, or phenyl and an inert carrier.

9. A composition according to claim 8 where R is alkyl.
10. A composition according to claim 8 where R is dodecyl.
11. A process for preparing compounds of the formula:

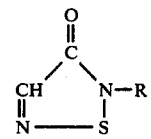

where R is an alkyl group of from 1 to 16 carbon atoms, benzyl or phenyl comprising reacting an amide of the formula:

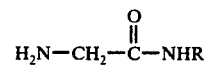

with at least one mole of a sulfur monohalide, $S_2X_2$, where X is bromine or chlorine, at a temperature of from $-10°$ to $60°$ C. for 10 to 18 hours.

12. A method of preparing compounds of the formula:

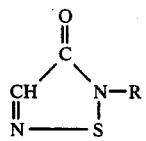

where R is a hydrocarbon of from 1 to 16 carbon atoms comprising reacting a mole of a compound of the formula:

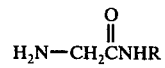

with from 2 to 5 moles of sulfur monohalide.

13. A compound according to claim 11 where R is propyl.
14. A compound according to claim 11 where R is isopropyl.

* * * * *